United States Patent
Tsuchimoto et al.

(10) Patent No.: US 10,939,855 B2
(45) Date of Patent: Mar. 9, 2021

(54) PHOTOELECTRIC SENSOR MODULE

(71) Applicant: Murata Manufacturing Co., Ltd., Nagaokakyo (JP)

(72) Inventors: Hirofumi Tsuchimoto, Nagaokakyo (JP); Kinichi Ito, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 166 days.

(21) Appl. No.: 15/916,382

(22) Filed: Mar. 9, 2018

(65) Prior Publication Data

US 2018/0192930 A1    Jul. 12, 2018

Related U.S. Application Data

(63) Continuation of application No. PCT/JP2016/075119, filed on Aug. 29, 2016.

(30) Foreign Application Priority Data

Sep. 11, 2015   (JP) .............................. JP2015-179000

(51) Int. Cl.
  *A61B 5/1455*   (2006.01)
  *A61B 5/0245*   (2006.01)
  *A61B 5/00*     (2006.01)

(52) U.S. Cl.
  CPC ........ *A61B 5/14552* (2013.01); *A61B 5/0245* (2013.01); *A61B 5/1455* (2013.01);
  (Continued)

(58) Field of Classification Search
  None
  See application file for complete search history.

(56) References Cited

U.S. PATENT DOCUMENTS

2014/0070077 A1    3/2014   Tsuchimoto et al.
2014/0081161 A1*   3/2014   Kuno ................ A61B 5/02438
                                                        600/502

(Continued)

FOREIGN PATENT DOCUMENTS

JP    02-111344 A    4/1990
JP    02-111345 A    4/1990

(Continued)

OTHER PUBLICATIONS

Official Communication issued in International Patent Application No. PCT/JP2016/075119, dated Nov. 15, 2016.

*Primary Examiner* — Marjan Fardanesh
(74) *Attorney, Agent, or Firm* — Keating & Bennett, LLP

(57) ABSTRACT

A photoelectric sensor module includes a first light emitting element that emits light having a first wavelength, a second light emitting element that emits light having a second wavelength different from the first wavelength, and a light receiving element that receives light emitted from the first light emitting element and reflected by an object and light emitted from the second light emitting element and reflected by the object are mounted on a substrate with linear edges. With respect to a virtual straight line defined on a surface of the substrate, a light emitting portion of the first light emitting element and a light emitting portion of the second light emitting element are line-symmetric, a light receiving portion of the light receiving element is line-symmetric, and a shape of the substrate in plan view is line-symmetric.

20 Claims, 9 Drawing Sheets

(52) U.S. Cl.
CPC ............ *A61B 5/6843* (2013.01); *A61B 5/725* (2013.01); *A61B 5/7225* (2013.01); *A61B 5/7246* (2013.01); *A61B 2562/0238* (2013.01); *A61B 2562/0242* (2013.01); *A61B 2562/043* (2013.01); *A61B 2562/185* (2013.01)

(56) References Cited

U.S. PATENT DOCUMENTS

| | | |
|---|---|---|
| 2014/0163342 A1 | 6/2014 | Shimuta et al. |
| 2015/0190079 A1 | 7/2015 | Yamaji et al. |
| 2016/0238439 A1 | 8/2016 | Chu et al. |
| 2016/0270708 A1 | 9/2016 | Tateda et al. |
| 2016/0338630 A1 | 11/2016 | Matsui et al. |

FOREIGN PATENT DOCUMENTS

| | | |
|---|---|---|
| JP | 05-21833 A | 1/1993 |
| JP | 10-216114 A | 8/1998 |
| JP | 5713103 B2 | 5/2015 |
| JP | 2016-036728 A | 3/2016 |
| WO | 2013/027359 A1 | 2/2013 |
| WO | 2014/045774 A1 | 3/2014 |
| WO | 2015/049963 A1 | 4/2015 |
| WO | 2015/115182 A1 | 8/2015 |

\* cited by examiner

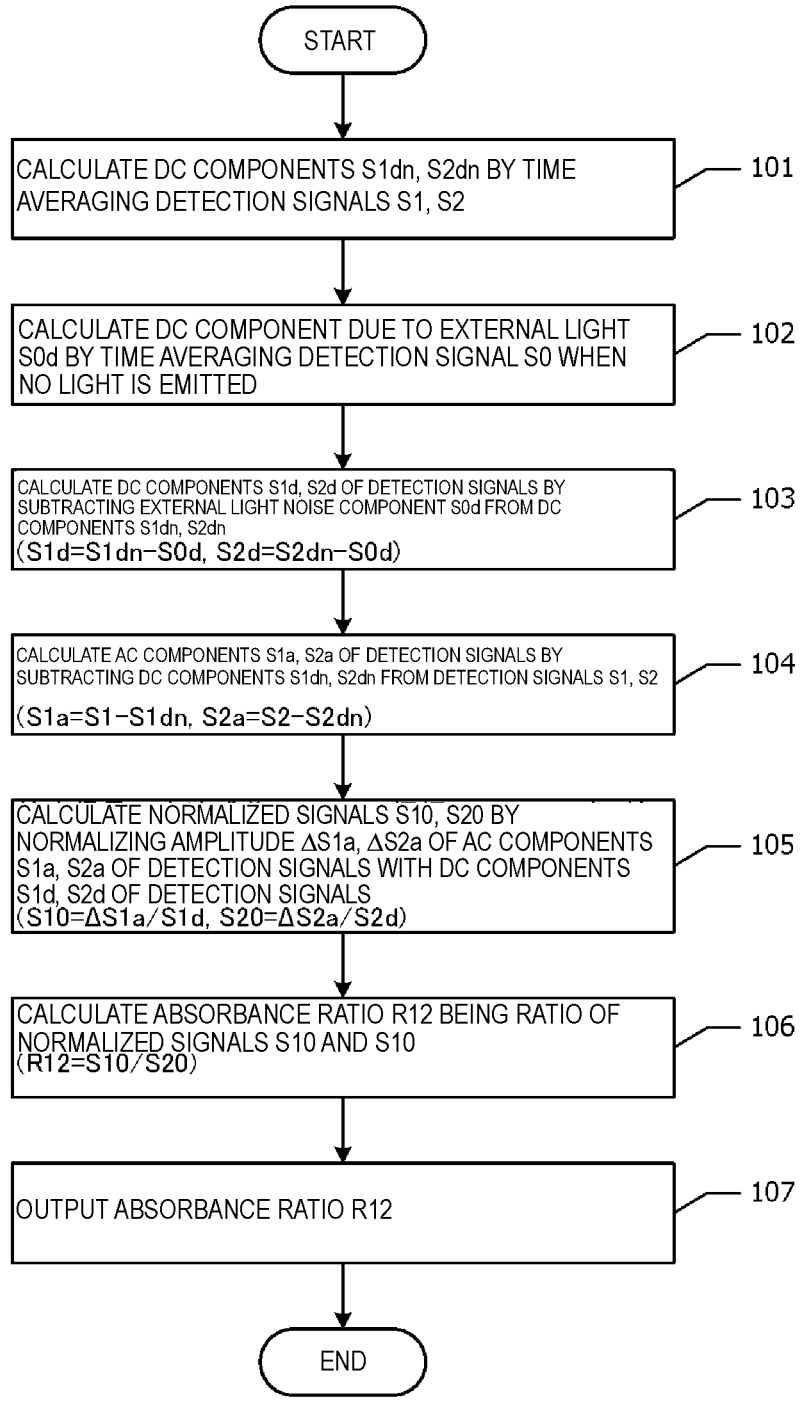

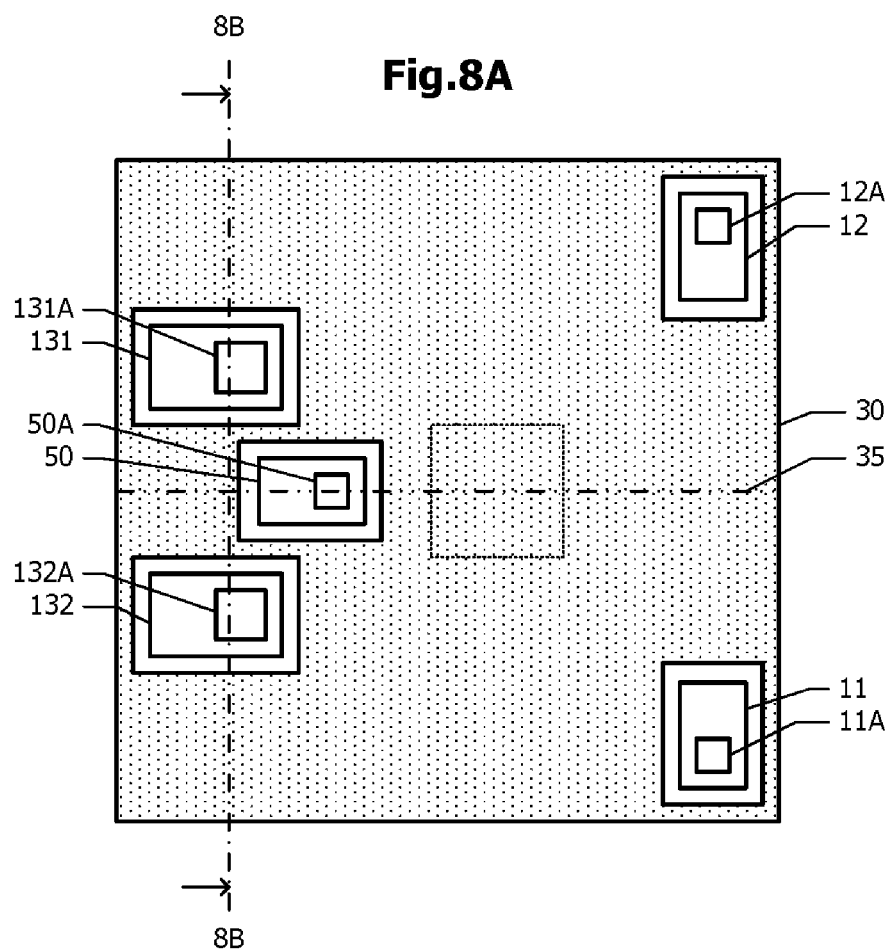
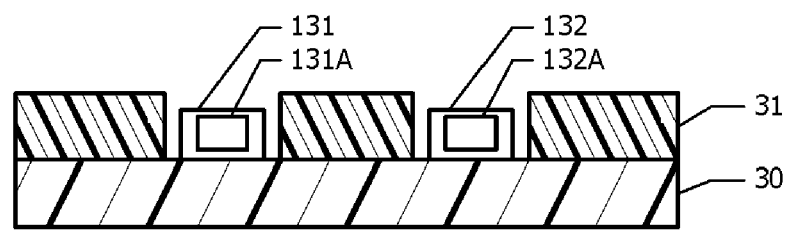

PHOTOELECTRIC SENSOR MODULE

CROSS REFERENCE TO RELATED APPLICATIONS

This application claims the benefit of priority to Japanese Patent Application No. 2015-179000 filed on Sep. 11, 2015 and is a Continuation Application of PCT Application No. PCT/JP2016/075119 filed on Aug. 29, 2016. The entire contents of each application are hereby incorporated herein by reference.

BACKGROUND OF THE INVENTION

1. Field of the Invention

The present invention relates to a photoelectric sensor module including a light emitting element and a light receiving element.

2. Description of the Related Art

Japanese Patent No. 5713103 discloses a light sensor device including a light emitter and a light receiver. The light emitter emits light towards a living body as an object to be measured. Light that passes through the object to be measured or is reflected by the object to be measured is received by a light receiving element. Based on an electrical signal outputted from the light receiving element, a photoplethysmographic signal corresponding to a pulse of the living body is obtained. In this light sensor device, an electrical signal photoelectrically converted by the light receiver is amplified by an amplifier. The amplified electrical signal is converted into a digital signal by an analog-to-digital converter. A computing unit performs various signal processing operations based on the digital signal.

Japanese Unexamined Patent Application Publication No. 2-111344 discloses a reflection oximeter. This reflection oximeter includes a plurality of first light emitting elements, a plurality of second light emitting elements, and a light receiving element. The first light emitting elements emit light having a first wavelength and the second light emitting elements emit light having a second wavelength, respectively. The first wavelength and the second wavelength are different from each other. The first light emitting element and the second light emitting element emit light towards a surface of a living body. Light reflected inside the living body is received by the light receiving element. Based on an intensity of the light received by the light receiving element, a degree of oxygen saturation in the blood may be obtained.

The plurality of first light emitting elements and the plurality of second light emitting elements are alternately arranged on the entire circumference of a circle having the same diameter with the light receiving element being positioned at a center. Even when a tissue of the living body is uneven, or when a housing in which the first light emitting element, or the like, is mounted is inclined, sufficient measurement accuracy is ensured because influence of the reflected light having the first wavelength on a signal intensity and influence of the reflected light having the second wavelength on a signal intensity are averaged.

In the reflection oximeter disclosed in Japanese Unexamined Patent Application Publication No. 2-111344, a plurality of first light emitting elements and a second light emitting elements need to be provided, and arranged along the circumference of the circle. Accordingly, it is difficult to reduce a cost of the mounted light emitting element.

A configuration in which the first light emitting element, the second light emitting element, and the light receiving element are mounted on the same substrate may be used. Since the first light emitting element and the second light emitting element are arranged along the circumference of the circle, a circular substrate is preferably used. Cutting a plurality of circular substrates out of a substrate for being cut into multiple pieces results in an unused area being left over. This results in a decrease in utilization efficiency of the substrate, and an increase in a cost of the substrate.

SUMMARY OF THE INVENTION

Preferred embodiments of the present invention provide photoelectric sensor modules with which it is possible to increase utilization efficiency of a multiple-piece substrate and to reduce a cost.

A photoelectric sensor module according to a preferred embodiment of the present invention includes a substrate with linear edges, a first light emitting element that is mounted on the substrate and emits light having a first wavelength, a second light emitting element that is mounted on the substrate and emits light having a second wavelength different from the first wavelength, and a light receiving element that receives light emitted from the first light emitting element and reflected by an object and light emitted from the second light emitting element and reflected by the object, wherein, with respect to a virtual straight line defined on a surface of the substrate, a light emitting portion of the first light emitting element and a light emitting portion of the second light emitting element are line-symmetric, a light receiving portion of the light receiving element is line-symmetric, and a shape of the substrate in plan view is line-symmetric.

It is possible to construct a substrate so as to have a shape in plan view capable of being arranged on a 2D plane without any unused area. This makes it possible to increase utilization efficiency of a multiple-piece substrate. In addition, since it is not necessary for the first light emitting elements and the second light emitting elements to be arranged along a circumference of a circle, it is possible to reduce a component cost and a manufacturing cost of the photoelectric sensor module. Being symmetric with respect to the virtual straight line makes it possible to equalize an influence of stray light due to light emitted from the first light emitting element and an influence of stray light due to light emitted from the second light emitting element. This makes it possible to increase the accuracy of calculating a degree of oxygen saturation.

A photoelectric sensor module according to a preferred embodiment of the present invention includes, in addition to the configuration of the photoelectric sensor module described above, a shielding film that covers an area of a surface of the substrate, none of the light emitting portion of the first light emitting element, the light emitting portion of the second light emitting element, and the light receiving portion of the light receiving element being located in the area, and that shields the light having the first wavelength and the light having the second wavelength, wherein a shape of the shielding film in plan view is line-symmetric with respect to the virtual straight line.

By configuring the shielding film to have a line-symmetric shape in plan view, an influence of stray light due to light emitted from the first light emitting element and an influence of stray light due to light emitted from the second light emitting element may be further equalized.

A photoelectric sensor module according to a preferred embodiment of the present invention includes, in addition to the configuration of the photoelectric sensor module described above, a pair of contact symmetry detecting elements mounted on the substrate, in which positions at which the pair of contact symmetry detecting elements are arranged are line-symmetric with respect to the virtual straight line, a distance from each of the contact symmetry detecting elements to the virtual straight line is longer than a distance from the light emitting portion of the first light emitting element to the virtual straight line, and each of the contact symmetry detecting elements defines a portion of a detection system that detects states of the contact symmetry detecting elements placed on the object, in a state in which a surface of the substrate on which the first light emitting element, the second light emitting element, and the light receiving element are mounted is in contact with the object.

A contact symmetry detecting element may be used to detect evenness of a state of a photoelectric sensor module placed on an object.

A photoelectric sensor module according to a preferred embodiment of the present invention includes, in addition to the configuration of the photoelectric sensor module described above, an arithmetic processor into which a detection signal corresponding to an intensity of light received by the light receiving element is input, in which the pair of contact symmetry detecting elements emit light having the same wavelength, the arithmetic processor compares an intensity of light emitted from one of the contact symmetry detecting elements, reflected by the object, and entering the light receiving element and an intensity of light emitted from the other contact symmetry detecting element, reflected by the object, and entering the light receiving element, and outputs a result of the comparison.

Comparing intensities of light entering the light receiving element enables evenness of a state of the photoelectric sensor module placed on the object to be determined.

In a photoelectric sensor module according to a preferred embodiment of the present invention, in addition to the configurations of the photoelectric sensor modules described above, the light receiving element includes a plurality of light receiving portions, and positions of the plurality of light receiving portions are line-symmetric with respect to the virtual straight line.

Intensities of light received by the plurality of light receiving portions may be converted from an analog signal to a digital signal by signal processing. A wide dynamic range may be provided as compared to a case in which analog-to-digital conversion of one intensity of strong light is performed.

A photoelectric sensor module according to a preferred embodiment of the present invention includes, in addition to the configuration of the photoelectric sensor module described above, a third light emitting element arranged on the virtual straight line, and an arithmetic processor into which detection signals corresponding to intensities of light received by the plurality of light receiving portions of the light receiving element are input, in which the arithmetic processor compares an intensity of light emitted from the third light emitting element, reflected by the object and received by one of the light receiving portions, and an intensity of light emitted from the third light emitting element, received by the other of the light receiving portions, and outputs a result of the comparison.

By comparing an intensity of light received by one of the light receiving portions and an intensity of light received by the other of the light receiving portions, it is possible to determine evenness of a state of the photoelectric sensor module placed on the object.

In a photoelectric sensor module according to a preferred embodiment of the present invention, in addition to the configuration of the photoelectric sensor module described above, the third light emitting element emits light having a wavelength shorter than both the first wavelength and the second wavelength.

A DC component of a detection signal of light having the wavelength shorter than both the first wavelength and the second wavelength tends to decrease, as compared to a DC component of a detection signal of light having the first wavelength and a detection signal of light having the second wavelength. This makes it easy to obtain the number of pulses from pulsation of the detection signal.

In a photoelectric sensor module according to a preferred embodiment of the present invention, in addition to the configurations of the photoelectric sensor modules described above, each of the first light emitting element and the second light emitting element includes a chip including the light emitting portion, and a package in which the chip is provided, and the package of the first light emitting element and the package of the second light emitting element are arranged to be line-symmetric with respect to the virtual straight line.

Since the packages are also line-symmetric, an influence of stray light due to light emitted from the first light emitting element and an influence of stray light due to light emitted from the second light emitting element may be further equalized.

A photoelectric sensor module according to a preferred embodiment of the present invention includes, in addition to the configurations of the photoelectric sensor modules described above, a motherboard on which the substrate is mounted, in which each of the first light emitting element and the second light emitting element includes a plurality of light emitting portions, and at least one of the light emitting portions of the first light emitting element and at least one of the light emitting portions of the second light emitting element are mounted on the motherboard.

A distance between the first light emitting element and the second light emitting element may be extended, without being restricted by a size of the substrate. In other words, a small substrate may be used even when a distance between the first light emitting element and the second light emitting element is increased. Thus, a reduction of a component cost is achieved.

With preferred embodiments of the present invention, it is possible to configure a substrate to have a shape in plan view capable of being arranged on a 2D plane without an unused area. This makes it possible to increase utilization efficiency of a multiple-piece substrate. In addition, since it is not necessary that a first light emitting element and a second light emitting element are arranged along a circumference of a circle, it is possible to reduce a component cost and a manufacturing cost of a photoelectric sensor module. Symmetry with respect to the virtual straight line makes it possible to equalize an influence of stray light due to light emitted from the first light emitting element and an influence of stray light due to light emitted from the second light emitting element. This makes it possible to increase the accuracy of calculating a degree of oxygen saturation.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 4 is a flowchart of signal processing executed by an arithmetic processor.

FIG. 8A is a plan view of a photoelectric sensor module according to Preferred Embodiment 4 of the present invention, and FIG. 8B is a cross-sectional view of FIG. 8A taken along a dot-dash line 8B-8B.

DETAILED DESCRIPTION OF THE PREFERRED EMBODIMENTS

Figure 1:
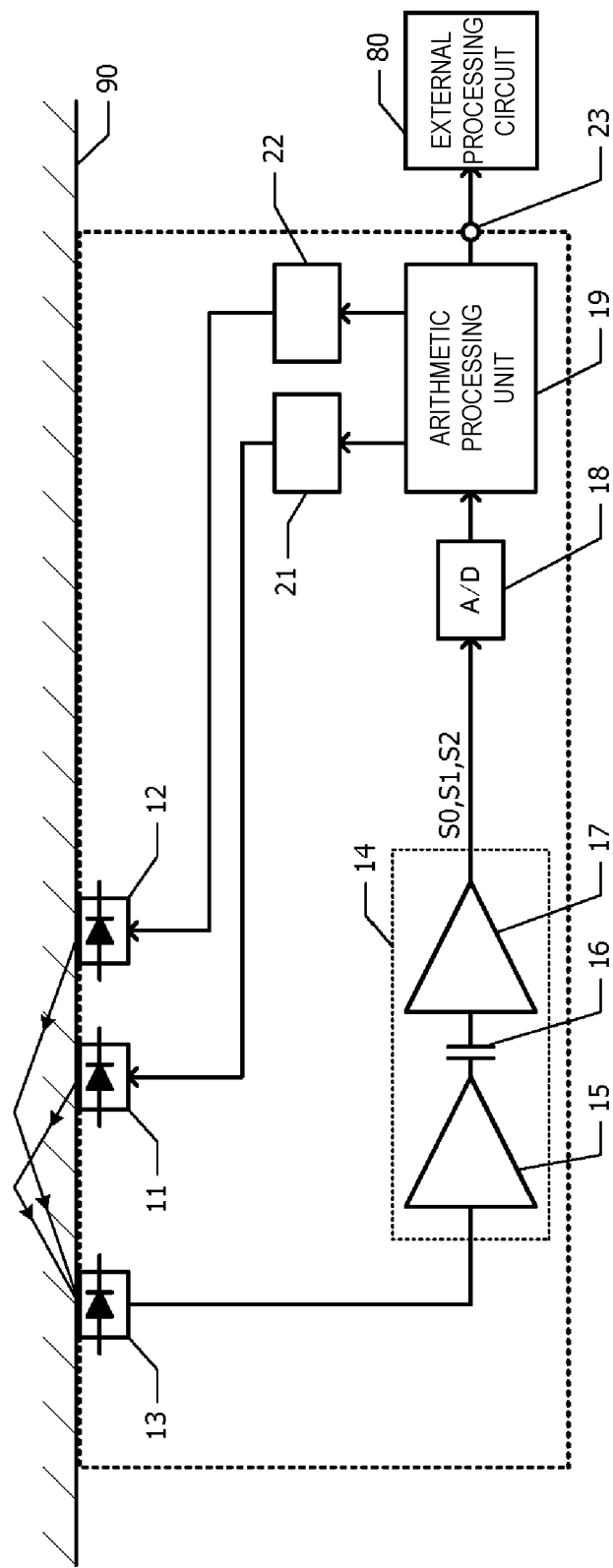
FIG. 1 is a block diagram of a photoelectric sensor module according to Preferred Embodiment 1 of the present invention.

A block diagram of a photoelectric sensor module according to Preferred Embodiment 1 of the present invention is illustrated in FIG. 1. A first light emitting element 11, a second light emitting element 12, and a light receiving element 13 are arranged to face an object 90. The first light emitting element emits light having a first wavelength and the second light emitting element 12 emits light having a second wavelength, with the wavelengths being different from each other. For example, the first light emitting element 11 preferably emits red light, for example, light in a range of about 700 nm band, and the second light emitting element 12 preferably emits infrared light, for example, light in a range of about 900 nm band. As the first light emitting element 11 and the second light emitting element 12, a light-emitting diode (LED) may preferably be used, for example. The object 90 is a portion of a living body, such as the fingertip or the earlobe, for example.

Driving currents are supplied to the first light emitting element 11 and the second light emitting element 12 from a first driving circuit 21 and a second driving circuit 22, respectively. The first light emitting element 11 and the second light emitting element 12 are controlled and emit pulsed light alternately with a constant frequency f. The frequency f is a sufficiently high value as compared to a pulse, for example, a value more than about ten times the pulse.

Light emitted from the first light emitting element 11 and light emitted from the second light emitting element 12 are reflected inside the object 90 and enter the light receiving element 13. The light receiving element 13 converts an intensity of the entered light into an electrical signal. A photodiode, a phototransistor, or other suitable element, for example, may preferably be used for the light receiving element 13.

An electrical signal outputted from the light receiving element 13 is input into an amplifier 14. The amplifier 14 amplifies the electrical signal and time-sequentially outputs detection signals S0, S1, and S2. The detection signal S0 indicates an intensity of light detected during a period in which both of the first light emitting element 11 and the second light emitting element 12 do not emit light. The detection signal S1 indicates an intensity of light detected during a period in which the first light emitting element 11 emits light. The detection signal S2 indicates an intensity of light detected during a period in which the second light emitting element 12 emits light.

The amplifier 14 includes a precedent amplifier 15, a coupling capacitor 16, and a subsequent amplifier 17. An output of the precedent amplifier 15 is input into the subsequent amplifier 17 via the coupling capacitor 16. The coupling capacitor 16 defines and functions as a high-pass filter allowing a signal of the frequency f to pass.

The detection signals S0, S1, and S2 are converted into digital signals by an analog-to-digital converter 18. An arithmetic processor 19 executes arithmetic processing for the analog-to-digital converted detection signals S0, S1, and S2. A result of the arithmetic processing is outputted to an external processing circuit 80 through an output terminal 23. Further, the arithmetic processor 19 controls the first driving circuit 21 and the second driving circuit 22. The external processing circuit 80 includes an image display device, and other suitable components.

Figure 2:
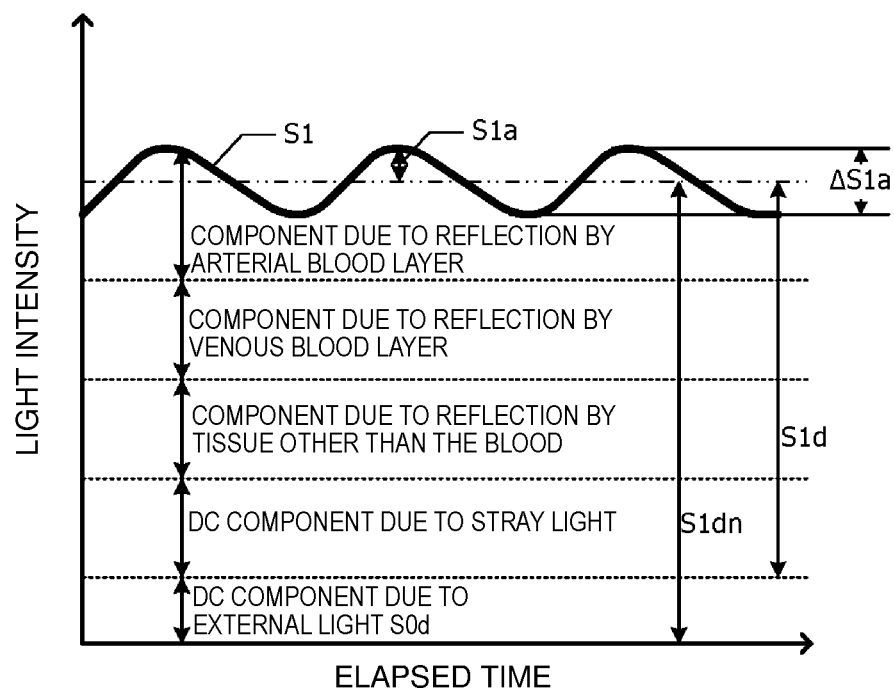
FIG. 2 is a graph illustrating an example of the change in an intensity of light received by a light receiving element over time.

FIG. 2 illustrates an example of change in an intensity of light received by the light receiving element 13 over time. A graph illustrated in FIG. 2 indicates an example of a case in which it is assumed that light is continuously emitted from the first light emitting element 11. The detection signal S1 by the light receiving element 13 includes a DC component due to external light S0$d$, a DC component due to stray light, a component due to reflection by a tissue other than the blood, a component due to reflection by a venous blood layer, and a component due to reflection by an arterial blood layer. The DC component due to stray light is caused by scattering on a substrate of a photoelectric sensor module or scattering in a housing. A light intensity of the component due to reflection by an arterial blood layer pulsates in response to a pulse.

A DC component of the detection signal S1 is denoted by S1$dn$. A DC component as a result of subtraction of a DC component due to external light S0$d$ from the DC component S1$dn$ is denoted by S1$d$. An AC component as a result of subtraction of the DC component S1$dn$ from the detection signal S1 is denoted by S1$a$. An amplitude of the AC component S1$a$ is denoted by $\Delta$S1$a$. In an actual measurement, the detection signal S1 is composed of a value obtained by sampling a wave form illustrated in FIG. 2 with the frequency f.

The detection signal S2 having a wave form similar to FIG. 2 is obtained, also in a case in which it is assumed that light is continuously emitted from the second light emitting element 12.

Figure 3A:
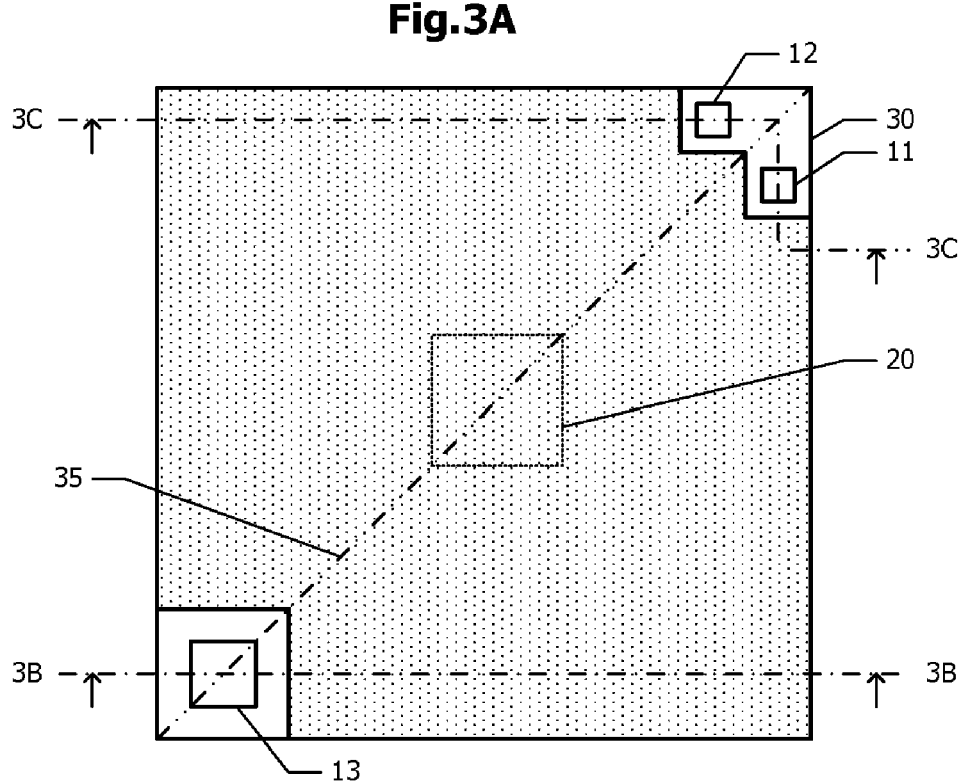
FIG. 3A is a plan view of the photoelectric sensor module according to Preferred Embodiment 1 of the present invention.
Figure 3B:
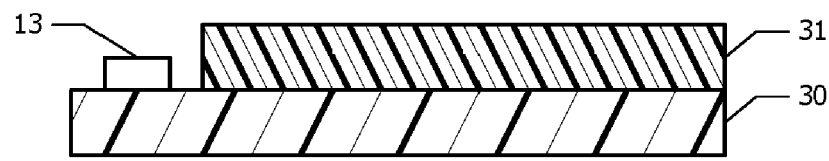
FIG. 3B and FIG. 3C are a cross-sectional view taken along a dot-dash line 3B-3B, and a cross-sectional view taken along a dot-dash line 3C-3C, respectively, of FIG. 3A.
Figure 3C:
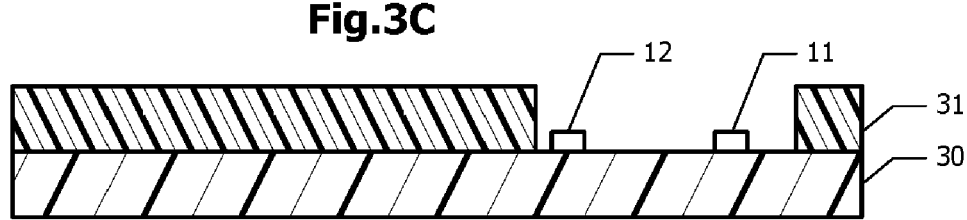

A configuration of the photoelectric sensor module according to Preferred Embodiment 1 is described with reference to the drawings in FIG. 3A to FIG. 3C. A plan view of the photoelectric sensor module according to Preferred Embodiment 1 is illustrated in FIG. 3A. FIG. 3B and FIG. 3C illustrate a cross-sectional view taken along the dot-dash line 3B-3B and a cross-sectional view taken along the dot-dash line 3C-3C, respectively, of FIG. 3A.

The first light emitting element 11, the second light emitting element 12, the light receiving element 13, and an electronic circuit component 20 are mounted on a non-circular substrate 30. A resin printed board, for example, may preferably be used for the substrate 30. The substrate 30 includes linear edges. For example, the shape of the substrate 30 is preferably square in plan view. The amplifier 14, the analog-to-digital converter 18, the arithmetic processor 19, the first driving circuit 21, and the second driving circuit 22, which are illustrated in FIG. 1 are defined by the electronic circuit component 20.

A surface-mounted light-emitting diode chip (LED chip), for example, may preferably be used for the first light emitting element 11 and the second light emitting element 12. A surface-mounted photodiode chip (PD chip), for example, may preferably be used for the light receiving element 13.

The shape of the substrate 30 in plan view is line-symmetric with respect to a virtual straight line 35 defined on a surface of the substrate 30. For example, the shape of the substrate 30 is preferably square in plan view, and the virtual straight line 35 corresponds to one diagonal of this square. A light emitting portion of the first light emitting element 11 and a light emitting portion of the second light emitting element 12 are preferably line-symmetric with respect to the virtual straight line 35. Here, it is not required that the two light emitting portions, including outer shapes thereof, are line-symmetric, and the two light emitting portions may be regarded to be "line-symmetric" as long as two center points of the light emitting portions are configured to be line-symmetrically positioned with respect to the virtual straight line 35. Note that, as described below, the two light emitting portions, including the outer shapes thereof, may preferably be configured to be line-symmetric with respect to the virtual straight line 35.

A light receiving portion of the light receiving element 13 is also preferably line-symmetric with respect to the virtual straight line 35. When the number of the light receiving portions is one, this light receiving portion is preferably located on the virtual straight line 35. Here, it is not required that the light receiving portion, including the outer shape thereof, is line-symmetric, and the light receiving portion may be regarded as "line-symmetric" as long as a center point of the light receiving portion is configured to be located on the virtual straight line. Note that, as described below, the outer shape of the light receiving portion may preferably be configured to be line-symmetric with respect to the virtual straight line 35.

An area of a mounted surface of the substrate 30, on which the light emitting portion of the first light emitting element 11, the light emitting portion of the second light emitting element 12, the light receiving portion of the light receiving element 13 are not provided, is covered with a resin shielding film 31. In FIG. 3A, an area on which the shielding film 31 is provided is illustrated with a dot pattern. The electronic circuit component 20 is embedded in the shielding film 31. The shielding film 31 shields light emitted from the first light emitting element 11 and having the first wavelength, and light emitted from the second light emitting element 12 and having the second wavelength. Black resin is preferably used for the shielding film 31, for example, to improve a light shielding effect. The shape of the shielding film 31 in plan view is preferably line-symmetric with respect to the virtual straight line 35.

A flowchart of signal processing executed by the arithmetic processor 19 (FIG. 1) is illustrated in FIG. 4. In step 101, the DC component $S1dn$ (FIG. 2) of the detection signal $S1$ (FIG. 2) is calculated by time averaging of the detection signal $S1$ when the first light emitting element 11 emits light. Similarly, the DC component $S2dn$ of the detection signal $S2$ is calculated by time averaging of the detection signal $S2$ when the second light emitting element 12 emits light.

In step 102, the DC component due to external light $S0d$ (FIG. 2) is calculated by time averaging of the detection signal $S0$ when no light is emitted.

In step 103, the DC component $Sid$ (FIG. 2) of the detection signal $S1$ is calculated by subtracting the DC component due to external light $S0d$ from the DC component $S1dn$. Similarly, the DC component $S2d$ of the detection signal $S2$ is calculated.

In step 104, the AC component $S1a$ (FIG. 2) of the detection signal $S1$ is calculated by subtracting the DC component $S1dn$ from the detection signal $S1$. Similarly, an AC component $S2a$ of the detection signal $S2$ is calculated.

In step 105, a normalized signal $S10$ when the first light emitting element 11 emits light is calculated, by normalizing the amplitude $\Delta S1a$ (FIG. 2) of the AC component $S1a$ of the detection signal $S1$ with the DC component $Sid$. Specifically, the normalized signal $S10$ is calculated by dividing $\Delta S1a$ by $Sid$. Similarly, a normalized signal $S20$ when the second light emitting element 12 emits light is calculated.

In step 106, an absorbance ratio $R12$ is calculated by dividing the normalized signal $S10$ by the normalized signal $S20$. In step 107, the absorbance ratio $R12$ is outputted to the external processing circuit 80 (FIG. 1) via the output terminal 23. The external processing circuit 80 is capable of determining a degree of oxygen saturation in the blood from the absorbance ratio $R12$, for example. A calculated value of the degree of oxygen saturation is displayed in a displaying device.

Next, advantageous effects obtained by the configuration according to Preferred Embodiment 1 will be described below. In Preferred Embodiment 1, the square substrate 30 instead of a circular substrate (FIG. 3A) is preferably provided. This makes it possible to cut the substrate 30 of the photoelectric sensor module out of a substrate for being cut to multiple pieces without any waste. Note that, a substrate that is capable of being arranged on a 2D plane without any unused area and that has a line-symmetric outer shape (in plan view) may be used as the substrate 30. For example, a substrate having a rectangular shape or a rhomboidal shape, besides a square shape, may be used.

In Preferred Embodiment 1, the single first light emitting element 11 emitting light having the first wavelength and the single second light emitting element 12 emitting light having the second wavelength are provided. This makes it possible to further reduce the cost as compared to a configuration in which a plurality of light emitting elements emitting light having the first wavelength and a plurality of light emitting elements emitting light having the second wavelength are provided, respectively.

In Preferred Embodiment 1, a distance from the light receiving element 13 to the first light emitting element 11 is preferably equal or substantially equal to a distance from the light receiving element 13 to the second light emitting element 12. Further, an influence of the substrate 30 and the shielding film 31 on light having the first wavelength from the first light emitting element 11 to the light receiving element 13, and an influence of the substrate 30 and the shielding film 31 on light having the second wavelength from the second light emitting element to the light receiving element 13 are equivalent or substantially equivalent. Thus, an influence of stray light due to scattering, reflection, and the like, by the substrate 30 or the shielding film 31 is equalized or substantially equalized for the first wavelength and the second wavelength. That is, the DC component due to stray light illustrated in FIG. 2 is the same or substantially the same for the first wavelength and the second wavelength. As a result, it is possible to increase the accuracy of calculating the degree of oxygen saturation.

The light emitting portion of the first light emitting element 11 and the light emitting portion of the second light emitting element 12, including the outer shapes thereof, are preferably line-symmetric with respect to the virtual straight line 35, in order to further reduce a difference between the DC component due to stray light of light having the first wavelength and the DC component due to stray light of light having the second wavelength.

Preferred Embodiment 2

Next, a photoelectric sensor module according to Preferred Embodiment 2 of the present invention will be described with reference to FIG. 5. Hereinafter, differences from Preferred Embodiment 1 illustrated in the drawings in FIGS. 1 through 4 will be described, and description of the same configurations will be omitted.

Figure 5:
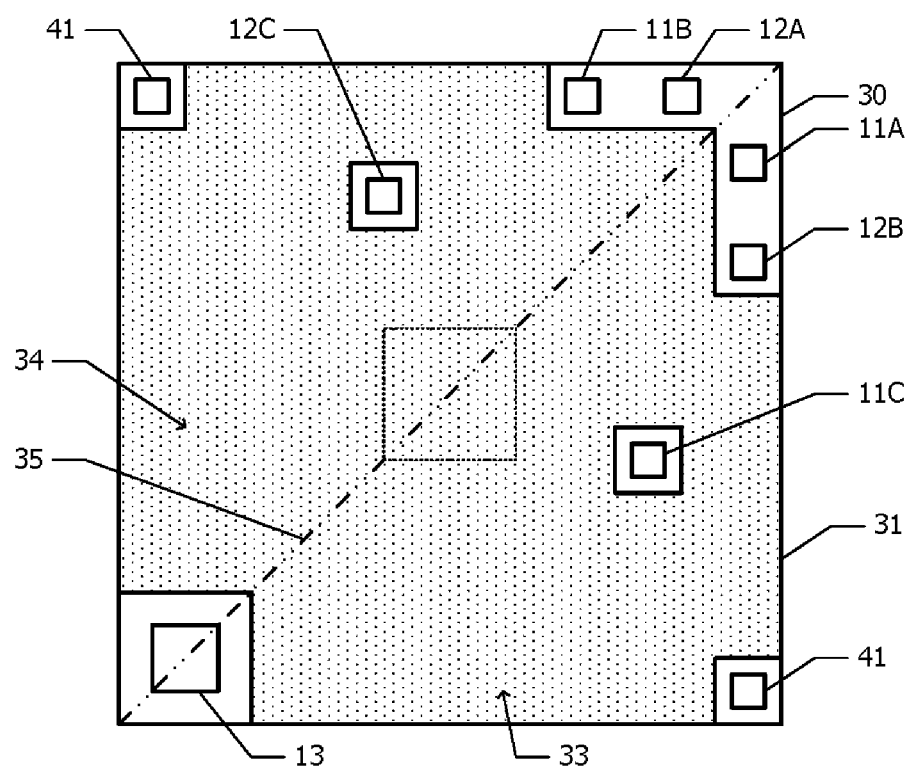
FIG. 5 is a plan view of a photoelectric sensor module according to Preferred Embodiment 2 of the present invention.

A plan view of the photoelectric sensor module according to Preferred Embodiment 2 is illustrated in FIG. 5. In Preferred Embodiment 1, the first light emitting element 11 emitting light having the first wavelength includes one light emitting portion, and the second light emitting element 12 emitting light having the second wavelength also includes one light emitting portion. In Preferred Embodiment 2, the first light emitting element 11 includes a plurality of light emitting portions 11A, 11B, and 11C, and the second light emitting element 12 also includes a plurality of light emitting portions 12A, 12B, and 12C. Each of the light emitting portions is preferably defined by an LED chip, for example.

Also, in Preferred Embodiment 2, the plurality of light emitting portions of the first light emitting element 11 and the plurality of light emitting portions of the second light emitting element 12 are line-symmetric with respect to the virtual straight line 35. For example, the light emitting portion 11A and the light emitting portion 12A are mounted in line-symmetrical positions, the light emitting portion 11B and the light emitting portion 12B are mounted in line-symmetrical positions, and the light emitting portion 11C and the light emitting portion 12C are mounted in line-symmetrical positions, with respect to the virtual straight line 35.

A mounted surface of the substrate 30 is partitioned into a first area 33 and a second area 34, with the virtual straight line 35 being a boundary therebetween. In FIG. 5, an example is illustrated in which the light emitting portions 11A, 11C, and 12B are provided in the first area 33, and the other light emitting portions 11B, 12A, and 12C are provided in the second area 34. Which one of the light emitting portions 11A and 12A in mutually line-symmetrical positions is to be provided in the first area 33 may be decided as appropriate. For example, all of the light emitting portions 11A, 11B, and 11C of the first light emitting element 11 may preferably be provided in the first area 33, and all of the light emitting portions 12A, 12B and 12C of the second light emitting element 12 may preferably be provided in the second area 34.

In addition, in Preferred Embodiment 2, a pair of contact symmetry detecting elements 41 are mounted on the substrate 30. Positions in which the pair of contact symmetry detecting elements 41 are provided are line-symmetric with respect to the virtual straight line 35. A distance from the contact symmetry detecting element 41 to the virtual straight line 35 is preferably longer than a longest distance from the first light emitting element 11 to the virtual straight line 35. The contact symmetry detecting element 41 defines a portion of a detection system that detects a state of the photoelectric sensor module placed on the object 90 (FIG. 1), in a state in which the mounted surface of the substrate 30 faces the object 90 and the photoelectric sensor module is made to contact with the object 90. For example, each of the pair of contact symmetry detecting elements 41 includes a light emitting element emitting light having the same or substantially the same wavelength.

The shielding film 31 covers an area of the mounted surface of the substrate 30 other than areas on which the plurality of light emitting portions 11A, 11B, and 11C of the first light emitting element 11; the plurality of light emitting portions 12A, 12B, and 12C of the second light emitting element 12; the light receiving portion of the light receiving element 13; and the pair of contact symmetry detecting elements 41 are provided. A shape of the shielding film 31 in plan view is preferably line-symmetric with respect to the virtual straight line 35, as in the case of Preferred Embodiment 1.

Advantageous effects obtained with the configuration of the photoelectric sensor module according to Preferred Embodiment 2 will be described below.

In Preferred Embodiment 2, it is possible to select any one of the plurality of light emitting portions 11A, 11B, and 11C of the first light emitting element 11, and to make only the selected light emitting portion emit light. Among the plurality of light emitting portions 12A, 12B, and 12C of the second light emitting element 12, one light emitting portion being line-symmetric with the selected light emitting portion of the first light emitting element 11 is made to emit light. In Preferred Embodiment 2, a plurality of combinations are possible as a pair of light emitting portions made to emit light to measure a degree of oxygen saturation.

When the DC component $S1dn$ of detected light illustrated in FIG. 2 exceeds a dynamic range of the analog-to-digital converter 18 (FIG. 1), it is not possible to measure the degree of oxygen saturation. In Preferred Embodiment 2, when a pair of light emitting portions being line-symmetric is made to emit light, and the DC component $S1dn$ or $S2dn$ exceeds the dynamic range of the analog-to-digital converter 18, the DC components $S1dn$ and $S2dn$ may fall within the dynamic range of the analog-to-digital converter 18 by making another pair of light emitting portions emit light in some cases. This makes it possible to reduce an occurrence frequency of an unmeasurable event.

Additionally, among the plurality of light emitting portions 11A, 11B, and 11C of the first light emitting element 11, two or more light emitting portions may be made to emit light at the same time. In this case, also among the light emitting portions 12A, 12B, and 12C of the second light emitting element 12, the corresponding two or more light emitting portions are made to emit light at the same time. When the plurality of light emitting portions of the first light emitting element 11 are made to emit light at the same time, averaged information of a wider area inside a living body is reflected on an intensity of light detected by the light receiving element 13. Thus, variations in detection results due to unevenness of locations of the blood vessels inside the object 90, or other variations, may be reduced.

In Preferred Embodiment 2, although the first light emitting element 11 includes the plurality of light emitting portions 11A, 11B, and 11C, and the second light emitting element 12 also includes the plurality of light emitting portions 12A, 12B, and 12C, these portions are not required to be arranged along a circumference of a circle with the light receiving portion being a center. This makes it possible to reduce the size of the photoelectric sensor module as compared with a configuration in which a plurality of light emitting portions is arranged along a circumference of a circle with a light receiving portion being a center.

When a state of the photoelectric sensor module placed on the object 90 (FIG. 1) is uneven (unbalanced) on both sides of the virtual straight line 35, variations occur between the influence of stray light due to light emitted from the first light emitting element 11 and the influence of stray light due to light emitted from the second light emitting element 12. With the configuration of the photoelectric sensor module according to Preferred Embodiment 2, it is possible to reduce these variations. Hereinafter, a method of reducing these variations will be described.

Among the plurality of light emitting portions 11A, 11B, and 11C of the first light emitting element 11, a farthest portion from the virtual straight line 35 is selected. Among the plurality of light emitting portions 12A, 12B, and 12C of the second light emitting element 12, the corresponding light emitting portion is selected. In an example illustrated in FIG. 5, the light emitting portion 11C of the first light emitting element 11 and the light emitting portion 12C of the second light emitting element 12 are selected.

The arithmetic processor 19 makes the light emitting portions 11C and 12C emit light, and compares the DC component $S1dn$ and the DC component $S2dn$. When a difference between these DC components exceeds a tolerable upper limit value, the state of the photoelectric sensor module placed on the object is regarded as being in an uneven state. The arithmetic processor 19 determines whether or not the difference between the DC component $S1dn$ and the DC component $S2dn$ exceeds the tolerable upper limit value. This determination result is outputted from the output terminal 23.

When the difference between the DC component $S1dn$ and the DC component $S2dn$ exceeds the tolerable upper limit value, an operator of the photoelectric sensor module adjusts the state of the photoelectric sensor module placed on the living body such that the difference between the DC component $S1dn$ and the DC component $S2dn$ does not exceed the tolerable upper limit value. This adjustment makes it possible to reduce variations in measurement results due to the influence of stray light.

Making the farthest light emitting portions 11C and 12C from the virtual straight line 35 emit light makes it easier to reflect unevenness, on both sides of the virtual straight line 35, in the state of the photoelectric sensor module placed on the object, on a detection signal. Since this detection signal is utilized to adjust the state of the photoelectric sensor module placed on the object, it is easier to ensure evenness in the state.

In Preferred Embodiment 2, it is possible to improve evenness in the state of the photoelectric sensor module placed on the object 90 using the contact symmetry detecting elements 41 (FIG. 5), while measurement portions are significantly improved or optimized. Hereinafter, a method for improving evenness in the state of the photoelectric sensor module placed on the object and for improving or optimizing measurement portions will be described.

The arithmetic processor 19 makes the pair of contact symmetry detecting elements 41 emit light with a time lag. When one of the contact symmetry detecting elements 41 emits light, a DC component is calculated based on a detection signal detected by the light receiving element 13. Also, when the other of the contact symmetry detecting elements 41 emits light, a DC component is calculated based on a detection signal detected by the light receiving element 13. The calculated values of the two DC components are compared and a result of the comparison is outputted from the output terminal 23.

A case in which detected values of the two DC components are the same or substantially the same suggests that the state of the photoelectric sensor module placed on the object 90 is even on both sides of the virtual straight line 35, and the blood vessels inside the object 90 are evenly distributed. An operator of the photoelectric sensor module adjusts the state of the photoelectric sensor module, and moves contact portions in order to equalize levels of the two DC components. This makes it possible to maintain a condition of receiving light emitted from the first light emitting element 11 and a condition of receiving light emitted from the second light emitting element 12 that are equivalent or substantially equivalent.

The pair of contact symmetry detecting elements 41 are arranged at positions farther from the virtual straight line 35, as compared to the first light emitting element 11 and the second light emitting element 12. This makes it easy to reflect unevenness on both sides of the virtual straight line 35 on a detection signal when making the contact symmetry detecting elements 41 emit light. Using the contact symmetry detecting elements 41 makes it easy to ensure evenness in measurement environments on both sides of the virtual straight line 35.

Preferred Embodiment 3

Next, a photoelectric sensor module according to Preferred Embodiment 3 of the present invention will be described with reference to FIGS. 6A, 6B and 7. Hereinafter, differences from Preferred Embodiment 1 will be described, and description of the same configurations will be omitted.

In Preferred Embodiment 1, preferably, an LED chip is used as the first light emitting element 11 and the second light emitting element 12, and a PD chip is used as the light receiving element 13. In Preferred Embodiment 3, preferably, a package LED is used as the first light emitting element 11 and the second light emitting element 12, and a package PD is used as the light receiving element 13.

Figure 6A:
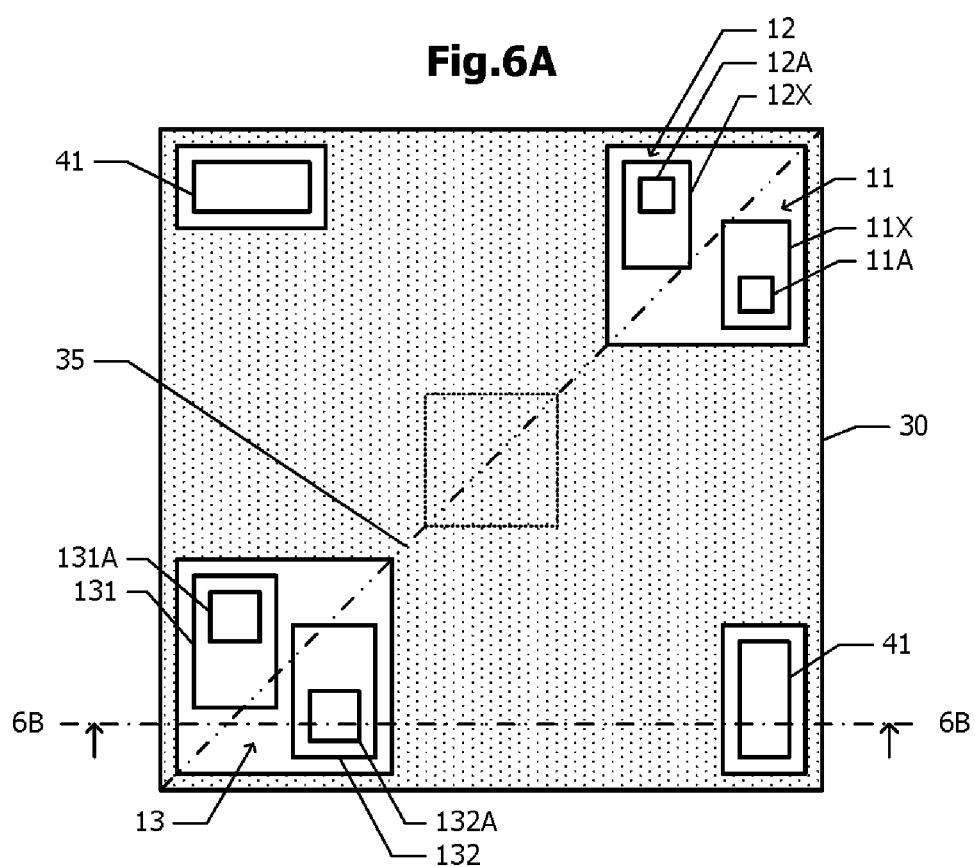
FIG. 6A is a plan view of a photoelectric sensor module according to Preferred Embodiment 3 of the present invention.
Figure 6B:
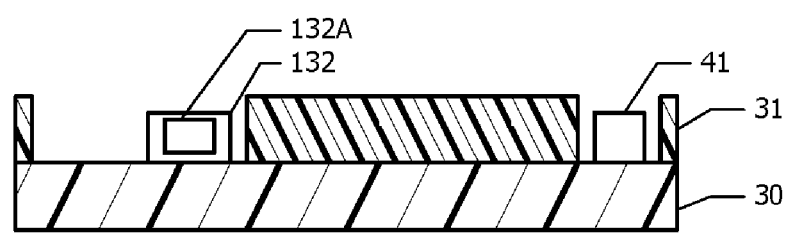
FIG. 6B is a cross-sectional view of FIG. 6A taken along a dot-dash line 6B-6B.

A plan view of the photoelectric sensor module according to Preferred Embodiment 3 is illustrated in FIG. 6A. FIG. 6B illustrates a cross-sectional view taken along a dot-dash line 6B-6B in FIG. 6A. A package LED 11X is used as the first light emitting element 11. The package LED 11X includes an LED chip including the light emitting portion 11A and a package in which the chip is provided. Similarly, a package LED 12X is also used as the second light emitting element 12. The package LED 12X includes an LED chip including the light emitting portion 12A and a package in which the chip is provided.

Also, in Preferred Embodiment 3, as in Preferred Embodiment 1, the light emitting portion 11A of the first light emitting element 11 and the light emitting portion 12A of the second light emitting element 12 are line-symmetric with respect to the virtual straight line 35. The package of the package LED 11X and the package of the package LED 12X are not always required to be line-symmetric with respect to the virtual straight line 35.

The light receiving element 13 includes a plurality of package PDs, for example, a first package PD 131 and a second package PD 132. The first package PD 131 includes a PD chip including a light receiving portion 131A and a package in which the chip is provided. Similarly, the second package PD 132 includes a PD chip including a light receiving portion 132A and a package in which the chip is provided.

The light receiving portion 131A and the light receiving portion 132A are line-symmetric with respect to the virtual straight line 35. A center point of the light receiving portion 131A and a center point of the light receiving portion 132A may preferably be configured to be in line-symmetric positions with respect to the virtual straight line 35, and the light receiving portion 131A and the light receiving portion 132A including outer shapes thereof may preferably be configured to be line-symmetric. The package of the first package PD 131 and the package of the second package PD 132 are not always required to be line-symmetric.

Also, in Preferred Embodiment 3, as in Preferred Embodiment 2, a pair of contact symmetry detecting elements 41 are mounted on the substrate 30. Although a light emitting element is preferably used for the contact symmetry detecting element 41 in Preferred Embodiment 2, a temperature sensor or a pressure sensitive sensor is preferably used in Preferred Embodiment 3.

Figure 7:
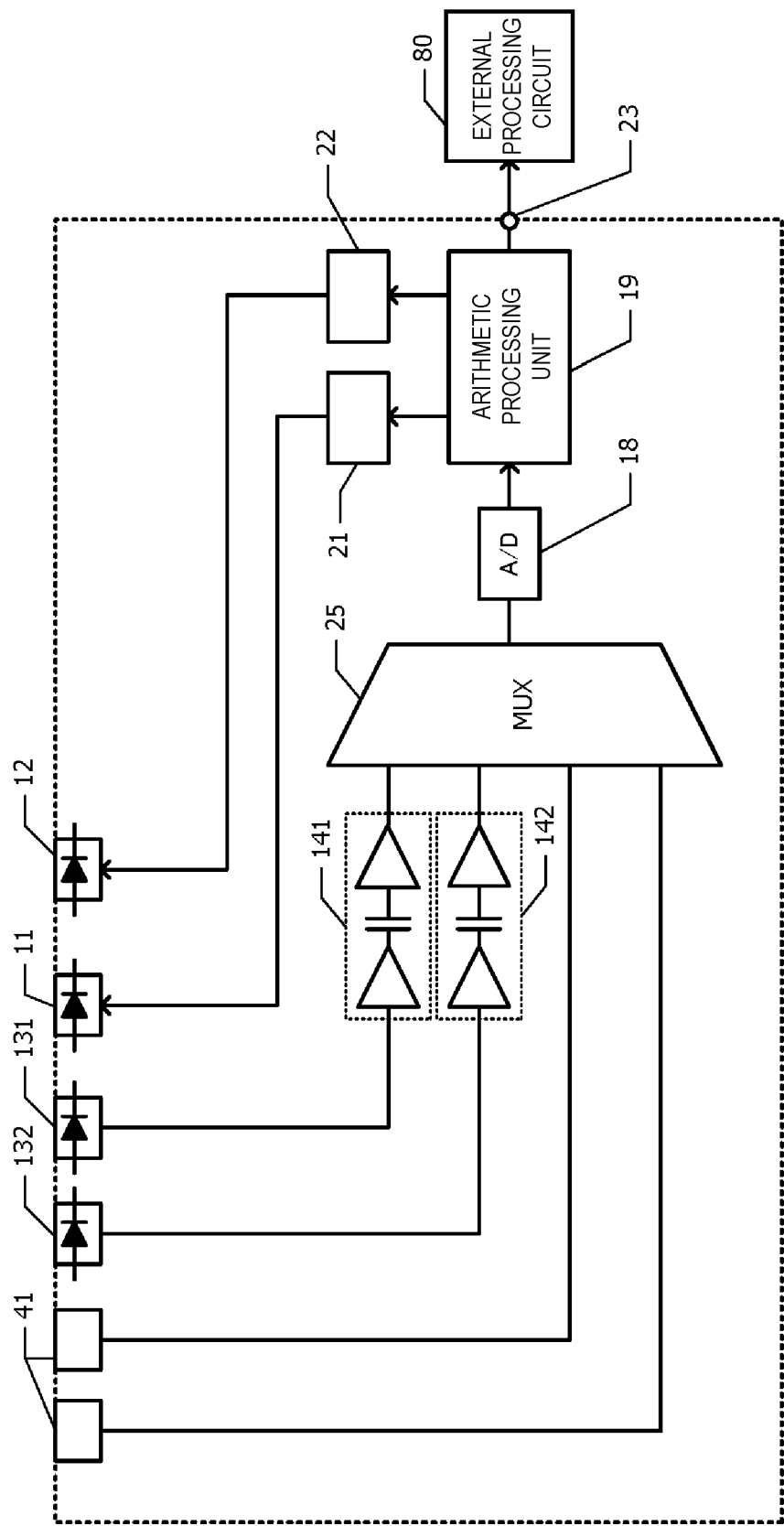
FIG. 7 is a block diagram of the photoelectric sensor module according to Preferred Embodiment 3 of the present invention.

A block diagram of the photoelectric sensor module according to Preferred Embodiment 3 is illustrated in FIG. 7. Hereinafter, differences from the block diagram of the photoelectric sensor module according to Preferred Embodiment 1 illustrated in FIG. 1 will be described, and description of the same configurations will be omitted.

A first amplifier 141 and a second amplifier 142 are provided for the first package PD 131 and the second package PD 132, respectively. Output signals from the first amplifier 141, the second amplifier 142, and the pair of contact symmetry detecting elements 41 are input into a multiplexer 25. The multiplexer 25 selects one signal from a plurality of input signals, and inputs the selected signal into the analog-to-digital converter 18. Note that, aside from the analog-to-digital converter 18 for output signals of the first amplifier 141 and the second amplifier 142, another analog-to-digital converter for output signals of the pair of contact symmetry detecting elements 41 may preferably be provided.

Advantageous effects obtained by the photoelectric sensor module according to Preferred Embodiment 3 will be described below.

Also, in Preferred Embodiment 3, as in Preferred Embodiment 1, a shape of the shielding film 31 (FIG. 6A) in plan view is preferably line-symmetric with respect to the virtual straight line 35. Further, in Preferred Embodiment 3, the light receiving portion 131A on one side and the light receiving portion 132A on the other side of the light receiving element 13 are line-symmetric with respect to the virtual straight line 35. Thus, the influence of the substrate 30 and the shielding film 31 on light having the first wavelength from the first light emitting element 11 to the light receiving element 13, and the influence of the substrate 30 and the shielding film 31 on light having the second wavelength from the second light emitting element 12 to the light receiving element 13 are equivalent or substantially equivalent. Thus, the influence of stray light due to scattering, reflection, and the like, by the substrate 30 or the shielding film 31 is equalized or substantially equalized for the first wavelength and the second wavelength. As a result, as in the case of Preferred Embodiment 1, it is possible to increase accuracy of calculating a degree of oxygen saturation.

A detection signal of the first package PD 131 and a detection signal of the second package PD 132 are separately input into the analog-to-digital converter 18 via the multiplexer 25, and are separately analog-to-digital converted. This makes it possible to ensure a dynamic range equivalent or substantially equivalent to a detection signal of the light receiving element 13 of Preferred Embodiment 1, for each of the first package PD 131 and the second package PD 132. Summing up the separately analog-to-digital converted two digital signals makes it possible to obtain the detection signals S1 and S2 (FIG. 2) indicating an intensity of light received by the light receiving element 13. Respective dynamic ranges of the detection signals S1 and S2 substantially expand as a result.

Comparing the detection signal of the first package PD 131 and the detection signal of the second package PD 132 makes it possible to obtain information on evenness (degree of balance) in the state of the photoelectric sensor module placed with the virtual straight line 35 being a center.

When a temperature sensor is used as the pair of contact symmetry detecting elements 41, it is possible to place the photoelectric sensor module on, for example, the chest of a living body, measure a degree of oxygen saturation, and measure a body temperature at the same time. Further, when the state of the photoelectric sensor module is uneven on both sides of the virtual straight line 35, a difference between a temperature measured by one of the contact symmetry detecting elements 41, and a temperature measured by the other of the contact symmetry detecting elements 41 increases. Thus, it is possible to determine a degree of balance in the state of the photoelectric sensor module on both sides of the virtual straight line 35 by comparing the respective temperatures detected by the pair of contact symmetry detecting elements 41.

For example, the arithmetic processor 19 evaluates the degree of balance in the state of the photoelectric sensor module based on a result of temperature comparison, and outputs a result of determination to the external processing circuit 80 from the output terminal 23. The external processing circuit 80 displays the result of determination on a display device. An operator of the photoelectric sensor module is able to optimize the state of the photoelectric sensor module placed on the object by reading the displayed contents.

When a pressure sensitive sensor is used as the pair of contact symmetry detecting elements 41, it is possible to determine a degree of balance in the state of the photoelectric sensor module on both sides of the virtual straight line 35 by comparing detected values of pressures.

Preferred Embodiment 4

Next, a photoelectric sensor module according to Preferred Embodiment 4 of the present invention will be described with reference to FIG. 8A and FIG. 8B. Hereinafter, differences from Preferred Embodiment 3 illustrated in FIGS. 6A through 7 will be described, and description of the same configurations will be omitted.

A plan view of the photoelectric sensor module according to Preferred Embodiment 4 is illustrated in FIG. 8A. FIG. 8B illustrates a cross-sectional view taken along a dot-dash line 8B-8B in FIG. 8A. In Preferred Embodiment 3, the virtual straight line 35 (FIG. 6A) being a line-symmetry reference is coincident with one diagonal of the substrate 30. In Preferred Embodiment 4, preferably, the virtual straight line 35 being a line-symmetry reference connects center points of a pair of edges facing each other of the substrate 30. A substrate having a rectangular shape may be used as the substrate 30.

A third light emitting element 50 is mounted in a position overlapping the virtual straight line 35. The third light emitting element 50 includes an LED chip including a light emitting portion 50A and a package in which the chip is provided. The third light emitting element 50 emits light having a third wavelength shorter than both of the first wavelength and the second wavelength from the light emitting portion 50A. For example, the third light emitting element 50 preferably emits green light.

In Preferred Embodiment 3, as illustrated in FIG. 6A, the light emitting portion 11A of the first light emitting element 11 and the light emitting portion 12A of the second light emitting element 12 are line-symmetric with respect to the virtual straight line 35, but the package of the first light emitting element 11 and the package of the second light emitting element 12 are not line-symmetric. Similarly, preferably, the light receiving portion 131A of the first package PD 131 and the light receiving portion 132A of the second package PD 132 are line-symmetric with respect to the virtual straight line 35, but the package of the first package PD 131 and the package of the second package PD 132 are not line-symmetric.

In comparison to this, in Preferred Embodiment 4, preferably, a package of the first light emitting element 11 and a package of the second light emitting element 12 are line-symmetric with respect to the virtual straight line 35. Additionally, a package of the first package PD 131 and a package of the second package PD 132 are preferably line-symmetric.

Next, advantageous effects obtained by the photoelectric sensor module according to Preferred Embodiment 4 will be described below.

In Preferred Embodiment 4, the first light emitting element 11 and the second light emitting element 12, including the packages thereof, are symmetric. Additionally, the first package PD 131 and the second package PD 132, including the packages, are symmetric. Thus, compared to Preferred Embodiment 3, it is possible to further improve evenness in the environment of respective propagation paths of light having the first wavelength emitted from the first light emitting element 11, and light having the second wavelength emitted from the second light emitting element 12. This makes it possible to increase accuracy of a result of measuring a degree of oxygen saturation.

By making the first package PD 131 and the second package PD 132 receive light emitted from the third light emitting element 50, and comparing intensities of the received light, it is possible to determine a degree of balance in the state of the photoelectric sensor module placed on the object.

When light having a wavelength shorter than that of red light, for example, green light, is used as light to be emitted toward a living body, a ratio of the DC component S1$dn$ to an amplitude $\Delta$S1$a$ of the AC component S1$a$ illustrated in FIG. 2 decreases. This makes it easy to obtain the number of pulses from pulsation of the detection signal.

Preferred Embodiment 5

Next, a photoelectric sensor module according to Preferred Embodiment 5 of the present invention will be described with reference to FIG. 9A and FIG. 9B. Hereinafter, differences from Preferred Embodiment 4 illustrated in FIG. 8A and FIG. 8B will be described, and description of the same configurations will be omitted.

Figure 9A:
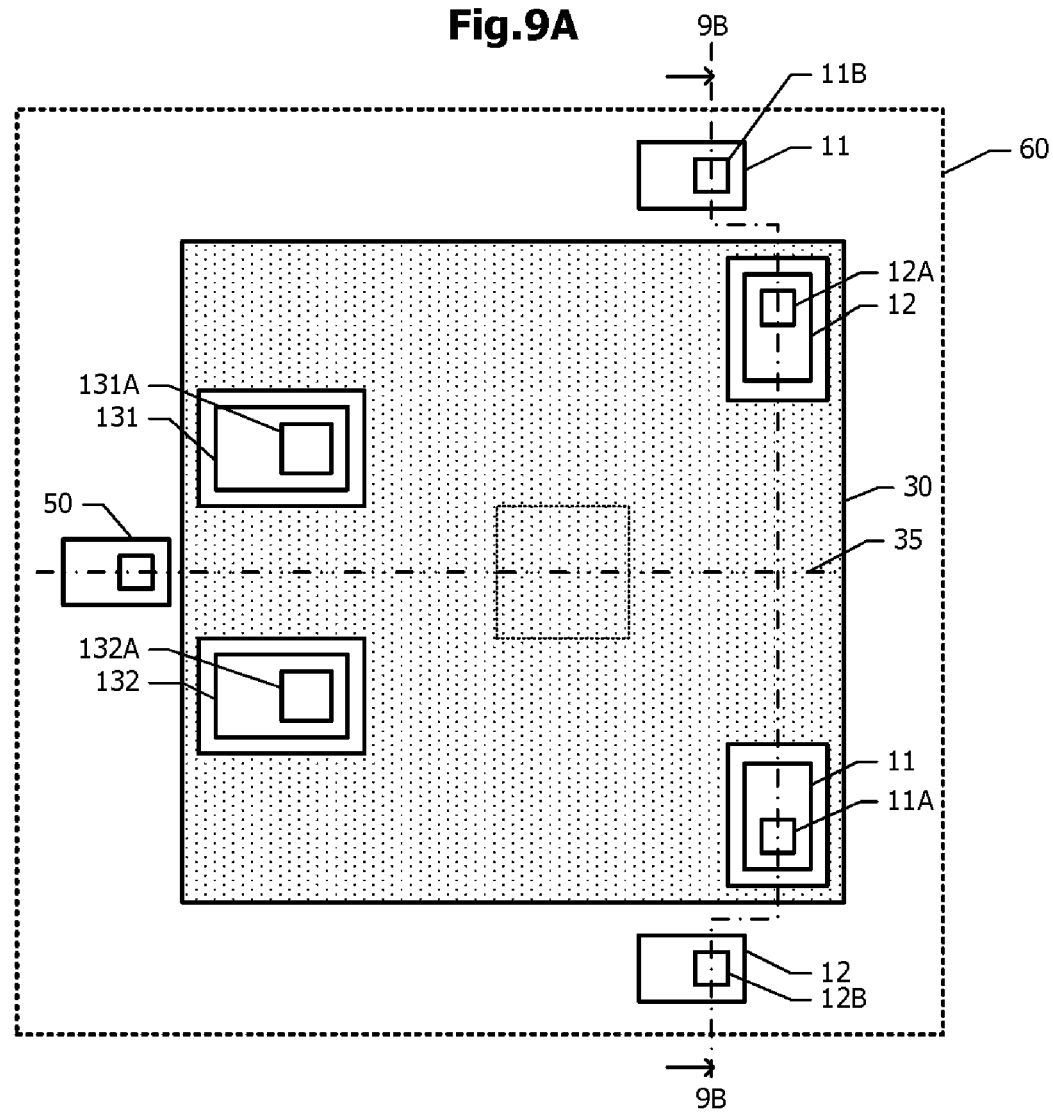
FIG. 9A is a plan view of a photoelectric sensor module according to Preferred Embodiment 5 of the present invention.
Figure 9B:
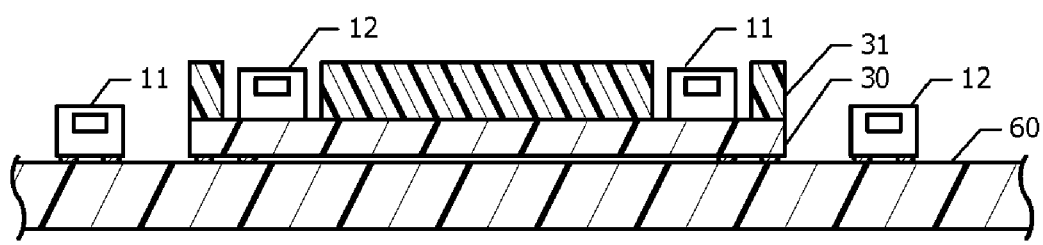
FIG. 9B is a cross-sectional view of FIG. 9A taken along a dot-dash line 9B-9B.

A plan view of the photoelectric sensor module according to Preferred Embodiment 5 is illustrated in FIG. 9A. FIG. 9B illustrates a cross-sectional view taken along a dot-dash line 9B-9B in FIG. 9A. The substrate 30 is mounted on a motherboard 60. In Preferred Embodiment 4, all of the first light emitting element 11, the second light emitting element 12, the third light emitting element 50, the first package PD 131, and the second package PD 132 are mounted on the substrate 30. In Preferred Embodiment 5, preferably the first light emitting element 11 includes a plurality of package LEDs, and some of the package LEDs are not mounted on the substrate 30, but instead, are mounted directly on the motherboard 60. Similarly, preferably the second light emitting element 12 also includes a plurality of package LEDs, and some of the package LEDs are mounted directly on the motherboard 60.

In an example illustrated in FIG. 9A, a package LED including the light emitting portion 11A of the first light emitting element 11 is mounted on the substrate 30, and a package LED including the light emitting portion 11B is mounted on the motherboard 60. A package LED including the light emitting portion 12A of the second light emitting element 12 is mounted on the substrate 30, and a package LED including the light emitting portion 12B is mounted on the motherboard 60. The light emitting portions 11A and 11B of the first light emitting element 11 and the light emitting portions 12A and 12B of the second light emitting element 12 are line-symmetric with respect to the virtual straight line 35, respectively. A package of the first light emitting element 11 and a package of the second light emitting element 12 are also preferably line-symmetric with respect to the virtual straight line 35.

The first package PD 131 and the second package PD 132 are, as in Preferred Embodiment 4 illustrated in FIGS. 8A and 8B, mounted on the substrate 30. The third light emitting element 50 is, unlike in the configuration of Preferred Embodiment 4, mounted on the motherboard 60. The third light emitting element 50 is positioned on the virtual straight line 35. That is, the third light emitting element 50 is line-symmetric with respect to the virtual straight line 35.

Also, in Preferred Embodiment 5, the same advantageous effects as those of Preferred Embodiment 4 are obtained. Additionally, in Preferred Embodiment 5, a distance between the light emitting portion 11B of the first light emitting element 11 and the light emitting portion 12B of the second light emitting element 12 may be increased, without being restricted by a size of the substrate 30. In other words, it is not necessary to increase the size of the substrate 30, in order to increase a distance between light emitting portions. This makes it possible to reduce the cost of the photoelectric sensor module.

The above-described preferred embodiments of the present invention are merely examples, and configurations described in different preferred embodiments may partially replace each other or be combined as well. The same or similar advantageous effects obtained by the same configurations in the plurality of preferred embodiments are not successively described in each of the preferred embodiments. Further, the present invention is not limited to the above-described preferred embodiments. For example, it will be apparent to those skilled in the art that various kinds of changes, improvements, combinations, and so on may be carried out.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A photoelectric sensor module, comprising:
a substrate with linear edges;
a first light emitting element that is mounted on the substrate and emits light having a first wavelength;
a second light emitting element that is mounted on the substrate and emits light having a second wavelength different from the first wavelength; and
a light receiving element that receives light emitted from the first light emitting element and reflected by an object and light emitted from the second light emitting element and reflected by the object; wherein
with respect to a virtual straight line defined on a surface of the substrate, a light emitting portion of the first light emitting element and a light emitting portion of the second light emitting element are line-symmetric, a light receiving portion of the light receiving element is line-symmetric, and a shape of the substrate in plan view is line-symmetric; and
each of the light emitting portion of the first light emitting element, the light emitting portion of the second light emitting element, and the light receiving portion of the light receiving element is exposed to ambient air from outside of the photoelectric sensor module.

2. The photoelectric sensor module according to claim 1, further comprising:
a shielding film that covers an area of a surface of the substrate in which none of the light emitting portion of the first light emitting element, the light emitting portion of the second light emitting element, and the light receiving portion of the light receiving element are provided, and that shields the light having the first wavelength and the light having the second wavelength; wherein
a shape of the shielding film in plan view is line-symmetric with respect to the virtual straight line.

3. The photoelectric sensor module according to claim 2, wherein the shielding film is made of black resin.

4. The photoelectric sensor module according to claim 1, further comprising:
a pair of contact symmetry detecting elements mounted on the substrate; wherein
positions at which the pair of contact symmetry detecting elements are provided are line-symmetric with respect to the virtual straight line, a distance from each of the contact symmetry detecting elements to the virtual straight line is longer than a distance from the light emitting portion of the first light emitting element to the virtual straight line; and
each of the contact symmetry detecting elements defines a portion of a detection system that detects states of the contact symmetry detecting elements placed on the object, in a state in which a surface of the substrate on which the first light emitting element, the second light emitting element, and the light receiving element are mounted is in contact with the object.

5. The photoelectric sensor module according to claim 4, further comprising:
an arithmetic processor into which a detection signal corresponding to an intensity of light received by the light receiving element is input; wherein the pair of contact symmetry detecting elements emit light having the same wavelength;
the arithmetic processor compares an intensity of light emitted from one of the contact symmetry detecting elements, reflected by the object, and entering the light receiving element and an intensity of light emitted from another contact symmetry detecting element, reflected by the object, and entering the light receiving element, and outputs a result of the comparison.

6. The photoelectric sensor module according to claim 4, further comprising:
an amplifier; wherein
an electrical signal outputted from the light receiving element is input into the amplifier; and
the amplifier amplifies the electrical signal outputs the detection signals.

7. The photoelectric sensor module according to claim 6, wherein the amplifier includes a precedent amplifier, a coupling capacitor, and a subsequent amplifier.

8. The photoelectric sensor module according to claim 7, wherein the coupler capacitor defines a high-pass filter.

9. The photoelectric sensor module according to claim 1, wherein the light receiving element includes a plurality of light receiving portions, and positions of the plurality of light receiving portions are line-symmetric with respect to the virtual straight line.

10. The photoelectric sensor module according to claim 9, further comprising:
a third light emitting element provided on the virtual straight line; and
an arithmetic processor into which detection signals corresponding to intensities of light received by the plurality of light receiving portions of the light receiving element are input; wherein
the arithmetic processor compares, an intensity of light emitted from the third light emitting element, reflected by the object and received by one of the light receiving portions, and an intensity of light emitted from the third light emitting element, reflected by the object and received by another of the light receiving portions, and outputs a result of the comparison.

11. The photoelectric sensor module according to claim 10, wherein the third light emitting element emits light having a wavelength shorter than both the first wavelength and the second wavelength.

12. The photoelectric sensor module according to claim 10, further comprising:
an amplifier; wherein
an electrical signal outputted from the light receiving element is input into the amplifier; and
the amplifier amplifies the electrical signal outputs the detection signals.

13. The photoelectric sensor module according to claim 12, wherein the amplifier includes a precedent amplifier, a coupling capacitor, and a subsequent amplifier.

14. The photoelectric sensor module according to claim 13, wherein the coupler capacitor defines a high-pass filter.

15. The photoelectric sensor module according to claim 1, wherein
each of the first light emitting element and the second light emitting element includes a chip including the light emitting portion, and a package in which the chip is provided; and
the package of the first light emitting element and the package of the second light emitting element are line-symmetric with respect to the virtual straight line.

16. The photoelectric sensor module according to claim 1, further comprising:
- a motherboard on which the substrate is mounted; wherein
- each of the first light emitting element and the second light emitting element includes a plurality of light emitting portions; and
- at least one of the light emitting portions of the first light emitting element and at least one of the light emitting portions of the second light emitting element are mounted on the motherboard.

17. The photoelectric sensor module according to claim 1, wherein
- each of the first light emitting element and the second light emitting element includes a chip including the light emitting portion, and a package in which the chip is provided; and
- the package of the first light emitting element and the package of the second light emitting element are not line-symmetric with respect to the virtual straight line.

18. The photoelectric sensor module according to claim 1, wherein the first light emitting element emits red light in a range of an approximately 700 nm band, and the second light emitting element emits infrared light in a range of an approximately 900 nm band.

19. The photoelectric sensor module according to claim 1, wherein the first light emitting element and the second light emitting element are light-emitting diodes.

20. The photoelectric sensor module according to claim 1, wherein the light receiving element is a photodiode or a phototransistor.

\* \* \* \* \*